US007241612B2

(12) United States Patent
Shapiro-Ilan et al.

(10) Patent No.: US 7,241,612 B2
(45) Date of Patent: Jul. 10, 2007

(54) METHODS AND MATERIALS FOR CONTROL OF INSECTS SUCH AS PECAN WEEVILS

(75) Inventors: David I. Shapiro-Ilan, Macon, GA (US); Wayne A. Gardner, Griffin, GA (US); Bruce Wood, Byron, GA (US); James R. Fuxa, Baton Rouge, LA (US)

(73) Assignee: The United States of America, as Represented by the Secretary of Agriculture, Washington, DC (US)

( * ) Notice: Subject to any disclaimer, the term of this patent is extended or adjusted under 35 U.S.C. 154(b) by 643 days.

(21) Appl. No.: 10/640,987

(22) Filed: Aug. 14, 2003

(65) Prior Publication Data

US 2004/0101516 A1 May 27, 2004

Related U.S. Application Data

(60) Provisional application No. 60/404,579, filed on Aug. 20, 2002, provisional application No. 60/428,023, filed on Nov. 21, 2002.

(51) Int. Cl.
*C12N 1/14* (2006.01)
(52) U.S. Cl. .................................. 435/254.1; 424/93.5
(58) Field of Classification Search ............. 435/254.1; 424/93.5
See application file for complete search history.

(56) References Cited

OTHER PUBLICATIONS

Feng, Z., et al., "Age-Specific Dose-Mortality Effects of *Beauveria bassiana* (Deuteromycotina: Hyphomycetes) on the European Corn Borer, *Ostrinia nubilalis* (lepidoptera: Pyralidae)", *J. Invertebrate Pathology*, vol. 46, pp. 259-264, (1985).
Shapiro-Ilan, D., et al., "Survey of Entomopathogenic Nematodes and Fungi Endemic to Pecan Orchards of the Southeastern United States and Their Virulence to the Pecan Weevil (Coleoptera: Curculionidae)", *Environmental Entomology*, vol. 32(1), pp. 187-195, (Feb. 2003).
Shapiro, D., et al., "Effects of Soil Type on Virulence and Persistence of Entomopathogenic Nematodes in Relation to Control of *Diaprepes abbreviatus* (Coleoptera: Curculionidae)", *Environmental Entomology*, vol. 29(5), pp. 1083-1087, (Oct. 2000).
Shapiro-Ilan, D., "Virulence of Entomopathogenic Nematodes to Pecan Weevil Larvae, *Curculio caryae* (Coleoptera: Curculionidae), in the Laboratory", *J. Economic Entomology*, vol. 94(1), pp. 7-13, (Feb. 2001).
Shapiro-Ilan D. , et al., "Factors affecting commercial success: case studies in cotton, turf, and citrus", *In* R. Gaugler,[ed.] Entomopathogenic Nematology, CABI, In press; Tanada Y., and H. K. Kaya, Insect Pathology, (1993), Academic Press, San Diego, CA.
Harris, M. K., Pecan weevil management considerations, pp. 66-73, *In* B. McCraw, E. H. Dean, and B. W. Wood [eds.], "Pecan industry: current situation and future challenges, third national pecan workshop proceedings", (1999), U.S. Department of Agriculture, Agricultural Research Service.
Dutcher, J. D., and J. A. Payne, The impact of pecan weevil control strategies on non-target arthropods, pp. 39-50, *In* W. W. Neel [ed], Pecan weevil: research perspective, (1985), Quail Ridge Press, Brandon, MS.
Harris, M. K., Pecan phenology and pecan weevil biology and management, pp. 51-58, *In* W. W. Neel [ed], Pecan weevil: research perspective, (1985), Quail Ridge Press, Brandon, MS.
Sikorowski, P. P., Pecan weevil pathology, pp. 87-101, *In* W. W. Neel [ed] Pecan weevil: Research perspective, (1985), Quail Ridge Press, Brandon, MS.
Fuxa, J. R., et al., Pathogens and microbial control of north American forest insect pests, Forest Health Technology Enterprise Team, (Aug. 1998), USDA Forest Service, Morgantwown, WV.
Ellis, H.C., et al., Georgia pecan pest management guide, University of Georgia Cooperative Extension Service Bulletin No. 841 (2000).
Nguyen, K., et al., "Identification of Entomopathogenic Nematodes in the Steinernematidae and Heterorhabditidae (Nemata: Rhabditida)", *J. Nematology*, vol. 28(3), pp. 286-300, (Sep. 1996).
McCoy, C., et al., "Entomopathogenic Nematodes and Other Natural Enemies as Mortality Factors for Larvae of *Diaprepes abbreviatus* (Coleoptera: Curculionidae)", *Biol. Control.*, vol. 19, pp. 182-190, (2000).
Tedders, W., et al., "Pecan Weevil: Suppression of Larvae with the Fungi *Metarhizium anisopliae* and *Beauveria bassiana* and the Nematode *Neoaplectana dutky*", *J. Economic Entomology*, vol. 66(3), pp. 723-725, (Jun. 1973).
Gottwald, T., et al., "Suppresion of Pecan Weevil (Coleoptera: Curculionidae) Populations with Entomopathogenic Fungi", *J. Environmental Entomology*, vol. 12(2), pp. 471-474, (Apr. 1973).
Zimmerman, G., "The *Galleria* Bait Method for Detection of Entomopathogenic Fungi in Soil", *J. Appl. Ent.*, vol. 102, pp. 213-215, (1986).
Harrison, R., et al., "Relative Susceptibility of Pecan Weevil Fourth Instars and Adults to Selected Isolates of *Beauveria bassiana*", *Biological Control*, vol. 3, pp. 34-38, (1993).

(Continued)

*Primary Examiner*—Leon B. Lankford, Jr.
*Assistant Examiner*—Susan E. Fernandez
(74) *Attorney, Agent, or Firm*—John D. Fado; G. Byron Stover

(57) ABSTRACT

A biopesticidal composition for controlling insects (e.g., pecan weevils, the *diaprepes* root weevil, fall armyworm, fire ants), containing an agriculturally acceptable carrier and an effective insect (e.g., pecan weevils, the *diaprepes* root weevil, fall armyworm, fire ants) biopesticidal amount of a fungus selected from the group consisting of *Beauveria bassiana* having the identifying characteristics of *Beauveria bassiana* NRRL 30593, *Metarhizium anisopliae* having the identifying characteristics of *Metarhizium anisopliae* NRRL 30594, *Beauveria bassiana* having the identifying characteristics of *Beauveria bassiana* NRRL 30601, *Beauveria bassiana* having the identifying characteristics of *Beauveria bassiana* NRRL 30600, or mixtures thereof. Also, a method for controlling insects (e.g., pecan weevils, the *diaprepes* root weevil, fall armyworm, fire ants), involving applying an effective insect biopesticidal amount of the composition to the insects or to the plants, areas or substrates infested with the insects.

14 Claims, 3 Drawing Sheets

OTHER PUBLICATIONS

McCoy, C., et al., "Application and Evaluation of Entomapathogens for Citrus Pest Control", pp. 577-595, L. A. Lacey and H. K. Kaya, Eds "Field Manual of Techniques in Invertebrate Pathology", (2000), Kluwer Academic Publishers, Dordrecht.

Goettel, M., et al., "Fungi", pp. 255-282, L. A. Lacey and H. K. Kaya, Eds "Field Manual of Techniques in Invertebrate Pathology", (2000), Kluwer Academic Publishers, Dordrecht.

Goetttel, M., et al., "Fungi: Hyphomycetes", pp. 213-249, *In* L. A. Lacey [ed.] Manual of techniques in insect pathology, (1997), Academic Press, San Diego.

Lacey, L., et al., "Initial Handling and Diagnosis of Diseased Insects", pp. 1-15, *In* L. A. Lacey [ed.] Manual of techniques in insect pathology, (1997), Academic Press, San Diego.

Humber, Richard A., "Fungi: Identification", pp. 153-185, *In* L. A. Lacey [ed.] Manual of techniques in insect pathology, (1997), Academic Press, San Diego.

Mizell, R. F., Risk rating: a fruitful Approach to management of the pecan weevil, pp. 69-78, *In* W. W. Neel [ed], Pecan weevil: research perspective, 1985, Quail Ridge Press, Brandon, MS.

Neel, W., et al., Rearing the Pecan Weevil in the Laboratory, pp. 79-86, *In* W. W. Neel [ed], Pecan weevil: research perspective, 1985, Quail Ridge Press, Brandon, MS.

Mortality of *D. abbreviatus* after Exposure to
Entomopathogenic Fungi

Mortality of Fire Ants after Exposure to *B. bassiana* NRRL 30593

Fig. 2

Mortality of Fire Ants after Exposure to M. anisopliae NRRL 30594

METHODS AND MATERIALS FOR CONTROL OF INSECTS SUCH AS PECAN WEEVILS

REFERENCE TO RELATED APPLICATION

This application claims the benefit of U.S. Provisional Application No. 60/404,579, filed 20 Aug. 2002, and U.S. Provisional Application No. 60/428,023, filed 21 Nov. 2002, which are incorporated herein by reference in their entirety.

BACKGROUND OF THE INVENTION

The present invention relates to a biopesticidal composition for controlling insects (e.g., pecan weevils, the *diaprepes* root weevil, fall armyworm, fire ants), containing an agriculturally acceptable carrier and an effective insect (e.g., pecan weevils, the *diaprepes* root weevil, fall armyworm, fire ants) biopesticidal amount of at least one fungus selected from *Beauveria bassiana* having the identifying characteristics of *Beauveria bassiana* NRRL 30593, *Metarhizium anisopliae* having the identifying characteristics of *Metarhizium anisopliae* NRRL 30594, *Beauveria bassiana* having the identifying characteristics of *Beauveria bassiana* NRRL 30601, *Beauveria bassiana* having the identifying characteristics of *Beauveria bassiana* NRRL 30600, or mixtures thereof. The present invention also relates to a method for controlling insects (e.g., pecan weevils, the *diaprepes* root weevil, fall armyworm, fire ants) involving applying an effective insect biopesticidal amount of the above composition to the insects or to the plants, areas or substrates infested with the insects.

Insect pests are a major problem for agriculture. For example, the pecan weevil, *Curculio caryae* (Horn), is a major pest of pecans throughout the Southeast United States (Mizell, R. F., Risk rating: A fruitful approach to management of the pecan weevil, pp. 69-78, In W. W. Neel [ed], Pecan weevil: research perspective, 1985, Quail Ridge Press, Brandon, Miss.). The insects have a two or three-year life-cycle (Harris, M. K., Pecan phenology and pecan weevil biology and management, pp. 51-58, In W. W. Neel [ed], Pecan weevil: research perspective, 1985, Quail Ridge Press, Brandon, Miss.). Adults emerge from soil in late July-August and then feed on and oviposit in the nuts. Larvae develop within the nut and fourth instars drop to the soil where they burrow to a depth of 8-25 cm. The following year approximately 90% of the larvae pupate and spend the next nine months in the soil as adults; the remaining 10% of the population spend two years in the soil as larvae emerging as adults in the third year.

Control recommendations for the pecan weevil currently consist solely of applications of chemical insecticides (e.g., carbaryl) to the tree canopy to suppress adults (Ellis, H. C., et al., Georgia pecan pest management guide, University of Georgia Cooperative Extension Service Bulletin No. 841 (2000); Harris, M. K., Pecan weevil management considerations, pp. 66-73, In B. McCraw, E. H. Dean, and B. W. Wood [eds.], Pecan industry: current situation and future challenges, third national pecan workshop proceedings, 1999, U.S. Department of Agriculture, Agricultural Research Service). Late season applications of carbaryl, however, can result in resurgence of damaging aphid populations because carbaryl suppresses certain aphid predators (e.g., coccinellids) but does not suppress the pecan aphid complex (Dutcher, J. D., and J. A. Payne, The impact of pecan weevil control strategies on non-target arthropods, pp. 39-50, In W. W. Neel [ed], Pecan weevil: research perspective, 1985, Quail Ridge Press, Brandon, Miss.). Due to the problems associated with aphid resurgence, as well as other environmental and regulatory concerns, research on developing alternative control strategies is warranted. Microbial control (i.e., use of entomopathogenic viruses, bacteria, protozoa, fungi, or nematodes) is one of the potential alternatives to current chemical insecticides.

Among entomopathogens of *C. caryae* studied thus far, certain Hyphomycetes fungi (i.e., *Beauveria bassiana* (Balsamo) Vuillemin and *Metarhizium anisopliae* (Metschnikoff) Sorokin) have shown the most promise as microbial control agents (Fuxa, J. R., et al., Pathogens and microbial control of north American forest insect pests, Forest Health Technology Enterprise Team, 1998, USDA Forest Service, Morgantwown, W. Va.; Gottwald, T. R., and W. L. Tedders, Suppression of pecan weevil (Coleoptera: Curculionidae) populations with entomopathogenic fungi, Environ. Entomol., 12: 471-474 (1983); Sikorowski, P. P., Pecan weevil pathology, pp. 87-101, In W. W. Neel [ed] Pecan weevil: Research perspective, 1985, Quail Ridge Press, Brandon, Miss.). Fungi in the class Hyphomycetes generally invade the insect host through the cuticle, replicate within the host's hemocoel, and form external conidiophores to disperse their spores (Tanada Y., and H. K. Kaya., Insect Pathology, 1993, Academic Press, San Diego, Calif.). The fungi *B. bassiana* and *M. anispoliae* are pathogenic to a wide variety of insects including a number of curculionid or other coleopteran pests (Tanada Y., and H. K. Kaya., Insect Pathology, 1993, Academic Press, San Diego, Calif.). Due to susceptibility to environmental extremes (e.g., low relative humidity, ultraviolet light, temperature), fungi are most successful when applied to soil or other "protected" environments (Fuxa, J. R., and Y. Tanada [eds.], Epizootiology of insect diseases, 1987, John Wiley and Sons, New York, N.Y.). Microbial control of *C. caryae* with these agents is most likely to be successful when fungi are applied to soil as a barrier treatment when larvae are dropping from nuts or when adults are emerging (Sikorowski, P. P., Pecan weevil pathology, pp. 87-101, In W. W. Neel [ed] Pecan weevil: Research perspective, 1985, Quail Ridge Press, Brandon, Miss.).

Some promising results have been reported in suppressing *C. caryae* with fungi (e.g.,>60% suppression) (Gottwald, T. R., and W. L. Tedders, Suppression of pecan weevil (Coleoptera: Curculionidae) populations with entomopathogenic fungi, Environ. Entomol., 12: 471-474 (1983); Tedders, W. L., et al., Pecan weevil: suppression of larvae with the fungi *Metarhizium anisopliae* and *Beauveria bassiana* and the nematode *Neoaplectana dutkyi*, J. Econ. Entomol., 66: 723-725 (1973)). However, other laboratory and field experiments indicate a lack of consistency (i.e., less than 35% suppression) (Harrison, R. D., et al., Relative susceptibility of pecan weevil fourth instars and adults to selected isolates of *Beauveria bassiana*, Biological Control, 3: 34-38 (1993)). Virulence can depend substantially on the strain or species of the particular entomopathogen being used (Shapiro-Ilan D. I., et al., Factors affecting commercial success: case studies in cotton, turf, and citrus, In R. Gaugler, [ed.] Entomopathogenic Nematology, CABI, In press; Tanada Y., and H. K. Kaya, Insect Pathology, 1993, Academic Press, San Diego, Calif.). Discovery of new strains or species of fungi may lead to enhanced potential for microbial control since susceptibility of *C. caryae* varies among species or strains of entomopathogenic fungi (Harrison, R. D., et al., Relative susceptibility of pecan weevil fourth instars and adults to selected isolates of *Beauveria bassiana*, Biological Control, 3: 34-38 (1993)).

SUMMARY OF THE INVENTION

The present invention relates to a biopesticidal composition for controlling insects (e.g., pecan weevils, the *diaprepes* root weevil, fall armyworm, fire ants) containing an agriculturally acceptable carrier and an effective insect (e.g., pecan weevils, the *diaprepes* root weevil, fall armyworm, fire ants) biopesticidal amount of at least one fungus selected from *Beauveria bassiana* having the identifying characteristics of *Beauveria bassiana* NRRL 30593, *Metarhizium anisopliae* having the identifying characteristics of *Metarhizium anisopliae* NRRL 30594, *Beauveria bassiana* having the identifying characteristics of *Beauveria bassiana* NRRL 30601, *Beauveria bassiana* having the identifying characteristics of *Beauveria bassiana* NRRL 30600, or mixtures thereof.

The present invention also relates to a biologically pure culture of *Beauveria bassiana* having all the identifying characteristics of *Beauveria bassiana* NRRL 30593, a biologically pure culture of *Metarhizium anisopliae* having all the identifying characteristics of *Metarhizium anisopliae* NRRL 30594, a biologically pure culture of *Beauveria bassiana* having all the identifying characteristics of *Beauveria bassiana* NRRL 30601, and a biologically pure culture of *Beauveria bassiana* having all the identifying characteristics of *Beauveria bassiana* NRRL 30600.

In addition, the present invention relates to a method for controlling insects (e.g., pecan weevils, the *diaprepes* root weevil, fall armyworm, fire ants), involving applying an effective insect biopesticidal amount of the above composition (or fungi) to the insects or to the plants, areas or substrates infested with the insects.

BRIEF DESCRIPTION OF THE DRAWINGS

FIG. 2 shows mortality of fire ants after exposure to *Beauveria bassiana* NRRL 30593.

DETAILED DESCRIPTION OF THE INVENTION

Figure 1:
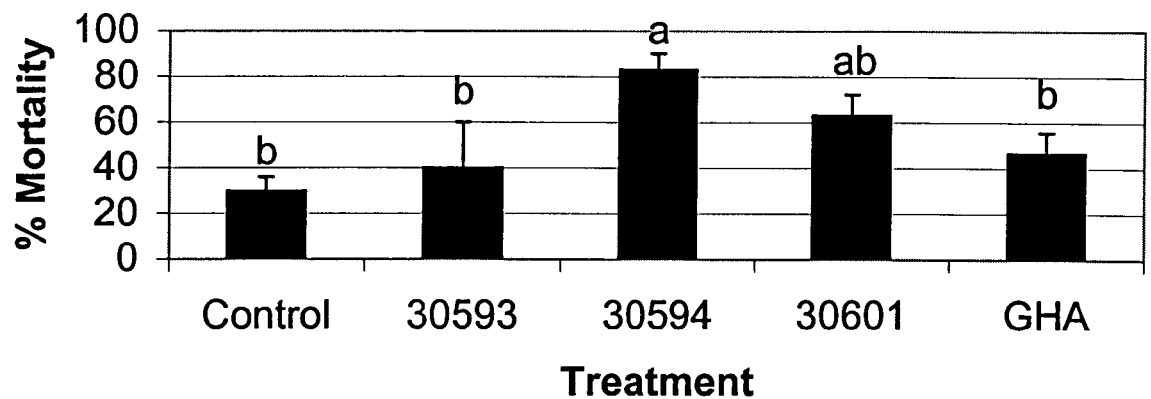
FIG. 1 shows mortality of *Diaprepes abbreviatus* after exposure to entomopathogenic fungi.
Figure 3:
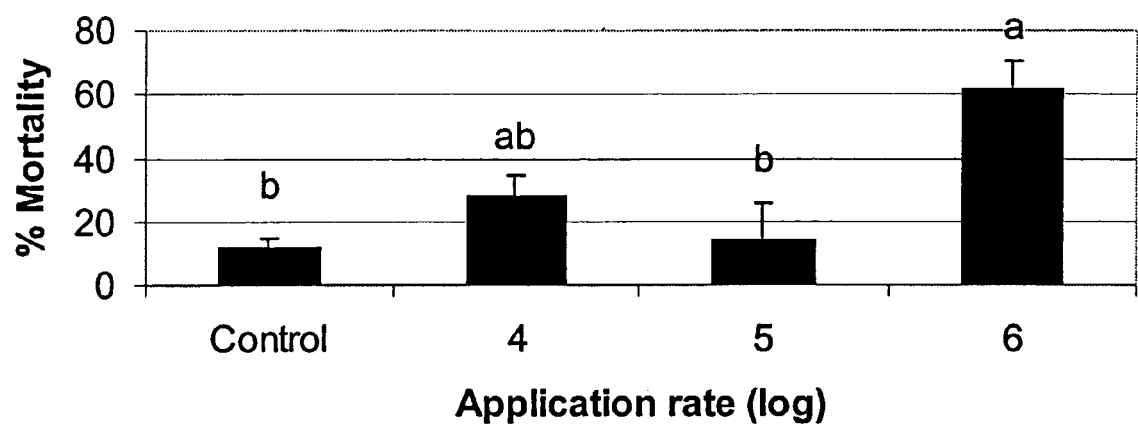
FIG. 3 shows mortality of fire ants after exposure to *Metarhizium anisopliae* NRRL 30594.

The present invention concerns a biologically pure culture of *Beauveria bassiana* having all the identifying characteristics of *Beauveria bassiana* NRRL 30593, a biologically pure culture of *Metarhizium anisopliae* having all the identifying characteristics of *Metarhizium anisopliae* NRRL 30594, a biologically pure culture of *Beauveria bassiana* having all the identifying characteristics of *Beauveria bassiana* NRRL 30601, and a biologically pure culture of *Beauveria bassiana* having all the identifying characteristics of *Beauveria bassiana* NRRL 30600. The terms "isolated", "purified", or "biologically pure" refer to material that is substantially or essentially free from components which normally accompany it as found in nature. The present invention also concerns a biologically pure culture of the combination of any two or more of the above fungi strains.

The present invention also concerns a biopesticidal composition for controlling insects (e.g., pecan weevils, the *diaprepes* root weevil, fall armyworm, fire ants), containing an effective insect (e.g., pecan weevils, the *diaprepes* root weevil, fall armyworm, fire ants) biopesticidal amount of at least one fungus selected from the group consisting of *Beauveria bassiana* having the identifying characteristics of *Beauveria bassiana* NRRL 30593, *Metarhizium anisopliae* having the identifying characteristics of *Metarhizium anisopliae* NRRL 30594, *Beauveria bassiana* having all the identifying characteristics of *Beauveria bassiana* NRRL 30601, *Beauveria bassiana* having all the identifying characteristics of *Beauveria bassiana* NRRL 30600, and mixtures thereof (e.g., any two or more of the above fungi), with or without an agriculturally acceptable carrier. The agriculturally acceptable carrier may be in the form of a liquid, powder, granules or small particles known in the art. Solid and liquid formulations may be used. Additional expedients used in the art, such as emulsifiers, thickeners, foaming agents, etc., may be used. The composition may also contain other chemical or biological control agents. The composition may also be applied, either simultaneously or sequentially, with other chemical or biological control agents. Application of the composition may be accomplished using standard operating equipment used in the agricultural or horticultural industry, for example by conventional ground spreaders or sprayers or aerially.

Those working in this field would of course be readily able to determine in an empirical manner (based on the teaching of this application) which organisms may be killed or eliminated by the fungi and biopesticidal compositions. Specifically exemplified herein is the use of fungi and biopesticidal compositions described herein to control pecan weevils and other insects including, for example, the following: white grubs (Scarabaeidae), e.g., *Phyllophaga* spp., *Cyclocephela* spp., *Popillia japonica*; other weevils (e.g., *Otiorhynchus* spp., *Diaprepes* spp., *Cosmopolites sordidus*, the *diaprepes* root weevil, *Diaprepes abbreviatus*); other Coleoptera (beetles) such as Chrysomelidae, e.g., the Colorado potato beetle, *Leptinotarsa decemlineata*, and *Diabrotica* spp.; aphids (Homoptera: Aphidae); other homopterans such as plant hoppers (e.g., Fulgoroidea such as *Nephotettix* spp.), Cercopidae, Cicadellidae, and Aleyrodidae; Lepidoptera, e.g., Noctuidae such as *Spodoptera* spp., *Helicoverpa zea*, *Agrotis ipsilon*, Pyralidae (e.g., *Ostrinia* spp.) and Geometridae; Orthoptera such as Acrididae and Gryllacrididae; mites (e.g., Eriophyidae, Tetranychidae); thrips; cockroaches; ticks (e.g., lxodidae); ants (e.g., fire ants, *Solenopsis* spp.); Fall armyworm, *Spodoptera frugiperda*. It is likely that the strains disclosed herein can also be used against the various pests discussed in L. A. Lacey and H. K. Kaya, Eds "Field Manual of Techniques in Invertebrate Pathology", 2000, Kluwer Academic Publishers, Dordrecht), and conditions of application may vary for application to suppress other insects (such as foliar sprays).

The fungi described herein may be employed in substantially the same manner as is customary for use of known fungal biocontrol agents. Application of the fungi in accordance with the present invention may be effected by a number of different procedures as are currently routinely employed for fungal biocontrol agents (e.g., Mycotrol® (*B. bassiana* GHA strain)). Further, it is contemplated as within the scope of the invention to apply the fungi with other components such as insecticides, attractants, pheromones, and feeding stimulants. The fungi can be applied using standard agricultural or horticultural equipment (e.g., see Goettel, M. S., Inglis, G. D., and Wraight, S. P., Fungi In "Field Manual of Techniques in Invertebrate Pathology", 2000, L. A. Lacey and H. K. Kaya, Eds., pp. 255-282, Kluwer Academic Publishers, Dordrecht), including pesticide sprayers or irrigation systems. Various formulations can be used, for example wettable powders or emulsifiable suspensions in association with sprays or lures.

The fungi used to practice the method of the present invention can be successfully grown on several different known media, for example potato dextrose agar (PDA), Sabouraud dextrose agar (SDA), oatmeal agar, and mixed bran agar. SDA provides an excellent medium for growing the fungi. The fungi used in the practice of the invention may be cultured and mass produced by known methods used to culture Beauveria and Metarhizium spp. See for example, U.S. Pat. Nos. 5,516,513 and 4,925,663; Microbial Control of Pest and Plant Diseases 1970-1980, published by Academic Press (1981, edited by H. D. Burges); and Feng et al., J. Invertebrate Pathology, Vol. 46, no. 3, November 1985, page 260. The fungal growth range is generally between 40° and 95° F. in a wide range of humidity with high humidity necessary to germinate spores and to increase spore production.

A wide range of application rates of the biopesticidal composition may be suitable in accordance with the present invention. Those working in this field would of course be readily able to determine in an empirical manner (based on the teaching of this application) the optimum rates of application for any given target organisms to be killed or eliminated. The amount of biopesticidal composition used will be at least an effective amount to reduce insect pests. The term "effective insect biopesticidal amount," as used herein, means the minimum amount of the biopesticidal composition needed to kill the target insects. The precise amount of the biopesticidal composition can easily be determined by one skilled in the art given the teaching of this application. The concentration of *Beauveria* and *Metarhizium* spp. used in the composition of the present invention is readily determinable by skilled practitioners depending, for example, on the extent and degree of infestation, time, weather conditions, life cycle of the pest, and concurrent use of other insecticides. Generally, $1 \times 10^{11}$ to $1 \times 10^{17}$ conidia per hectare is sufficient to control insect pests (e.g., pecan weevils, the *diaprepes* root weevil, fall armyworm, fire ants). A wide range of timing of application of the fungi may be suitable in accordance with the present invention. Those working in this field would of course be readily able to determine in an empirical manner (based on the teaching of this application) the optimum timing of application for any given combination of target organisms to be killed or eliminated.

Specifically, for pecan weevils, the fungi would generally be applied to soil or the tree trunk in the fall for targeting larvae, or in late summer or early fall if adult weevils are targeted. Depending on the environmental conditions and level of insect control desired the rate of application may vary greatly, e.g., from $1 \times 10^{11}$ to $1 \times 10^{17}$ conidia per hectare.

Biologically pure cultures of *Beauveria bassiana* strain BbGA2, *Metarhizium anisopliae* strain MaLA4, *Beauveria bassiana* strain BbMS1, and *Beauveria bassiana* strain BbLA3 have been deposited at the Agricultural Research Service Culture Collection (NRRL), 1815 North University Street, Peoria, Ill. 61604, USA, under the provisions of the Budapest Treaty. The deposit information and accession numbers are as follows:

| Culture | Accession Number | Deposit Date |
| --- | --- | --- |
| *Beauveria bassiana* strain BbGA2 | NRRL 30593 | May 31, 2002 |
| *Metarhizium anisopliae* strain MaLA4 | NRRL 30594 | May 31, 2002 |
| *Beauveria bassiana* strain BbMS1 | NRRL 30601 | Jul. 2, 2002 |
| *Beauveria bassiana* strain BbLA3 | NRRL 30600 | Jul. 2, 2002 |

The subject cultures have been deposited under conditions that assure that access to the cultures will be available during the pendency of this patent application to one determined by the Commissioner of Patents and Trademarks to be entitled thereto under 37 CFR 1.14 and 35 U.S.C. 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action. Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of a deposit, and in any case, for a period of at least thirty (30) years after the date of deposit or for the enforceable life of any patent which may issue disclosing the cultures. The depositor acknowledges the duty to replace the deposit(s) should the depository be unable to furnish a sample when requested, due to the condition of a deposit. All restrictions on the availability to the public of the subject culture deposits will be irrevocably removed upon the granting of a patent disclosing them.

The following examples are intended only to further illustrate the invention and are not intended to limit the scope of the invention as defined by the claims.

Materials and Methods:

Isolation of Entomopathogens: Twenty-one pecan orchards (varieties included Stuart, Schley, and Desirable) were surveyed in Arkansas, Georgia, Louisiana, and Mississippi. In each orchard five sample sites were chosen approximately 50 m from the next. Within each site, two sub-samples consisting of approximately two liters of soil were removed by shovel (to depth of 30 cm) from each of two adjacent trees (four sub-samples total per site). One half of the sub-samples were taken 25 cm from the trunk of the tree and the other half 2 m from the trunk. The sub-samples from each site were combined into a single plastic bag and mixed thoroughly. Approximately one half of the soil from each site (41) was removed, placed in a refrigerated cooler, and taken to the laboratory for processing.

Pathogens were isolated by the insect-baiting method (Zimmermann, G., The '*Galleria* bait method' for detection of entomopathogenic fungi in soil, J. Appl. Ent., 102-213-215 (1986)). In the laboratory, soil samples from each site were split into two plastic pots. Ten last instar greater waxmoth larvae, *Galleria mellonella* (L.) (obtained from Sunfish Bait Co., Webster, Wis.) were added to one pot and five *C. caryae* larvae to the other. Entomopathogens were isolated using both hosts because some species or strains can be host-specific; e.g., *Steinernema scapterisci* Nguyen and Smart shows considerable specificity to *Scapteriscus* spp. (Nguyen. K. B., and G. C. Smart Jr., Identification of entomopathogenic nematodes in the Steinemematidae and Heterorhabditidae (Nemata: Rhabditida), J. Nematol., 28:286-300 (1990)). Dead insects were removed from pots and replaced with healthy ones every five days for 15 days. Soil was kept moist (approximately at field capacity) during this period. Insect cadavers exhibiting signs of entomopathogenic fungus infection were purified on Sabouraud Dextrose Agar (fungi) for isolation (Tanada Y., and H. K. Kaya, Insect Pathology (1993), Academic Press, San Diego, Calif.; Goetttel, M. S., and D. Inglis, Fungi: Hyphomycetes, pp. 213-249, In L. A. Lacey [ed.] Manual of techniques in insect pathology, 1997, Academic Press, San Diego). The pathogenicity of fungi was confirmed through Koch's postulates (Lacey, L. A., and W. M. Brooks, Initial handling and diagnosis of diseased insects, pp. 1-15, In L. A. Lacey [ed.] Manual of techniques in insect pathology, 1997, Academic Press, San Diego). Entomopathogenic fungi were identified according to procedures described by Humber (Humber, R. A., Fungi: identification, pp. 153-185, In L. A. Lacey [ed.] Manual of techniques in insect pathology, 1997, Academic Press, San Diego).

Virulence Assays: Fungi were cultured on Sabouraud Dextrose Agar (Goetttel, M. S., and D. Inglis, Fungi: Hyphomycetes, pp. 213-249, In L. A. Lacey [ed.] Manual of techniques in insect pathology, 1997, Academic Press, San Diego). Before experimentation, fungi were stored at 4° C. and 13° C. for less than two and six weeks, respectively. Sub-culturing of fungi did not exceed three passages in the host or on agar before use in experiments.

Virulence experiments were conducted in plastic cups (Bioserv Inc., Frenchtown, N.J.) based on procedures previously described (Harrison, R. D., et al., Relative susceptibility of pecan weevil fourth instars and adults to selected isolates of *Beauveria bassiana*, Biological Control, 3: 34-38 (1993)). Cups (3-4 cm i.d., 3.5 cm deep) contained oven-dried soil from the USDA-ARS pecan orchard (Byron, Ga.) and contained one larva each. Cups in fungus experiments contained 10 g of soil. The soil was a loamy sand with the percentage sand:silt:clay=84:10:6, pH=6.1, and organic matter=2.8% by weight. Pecan weevil larvae ($4^{th}$ instar), collected from infested nuts on the USDA-ARS Research Station (Byron, Ga.), were stored in sterile (autoclaved) soil at 25° C. for two weeks, at which time diseased larvae were removed. Remaining larvae were then stored at 4°-10° C. until use (Shapiro-Ilan, D. I., Virulence of entomopathogenic nematodes to pecan weevil larvae *Curculio caryae* (Coleoptera: Curculionidae) in the laboratory, J. Econ. Entomol., 94: 7-13 (2001)).

It was not feasible to include all fungal isolates in a single experiment. Therefore, the isolates were tested in a series of assays, which included at least two common isolates in each test for comparison. The fungi experiments were split into four assays (hereafter referred to as Assays 3-6). All isolates were tested except BbGA5 and MaLA1 because these cultures were inadvertently lost prior to experimentation. Each assay contained three replicates of 10 cups per treatment (isolate) and was conducted twice (two trials). All fungus experiments included Mycotrol® (*B. bassiana* GHA strain), which is currently registered for pecan weevil control by Emerald BioAgriculture Corp. as a standard, and the new isolate BbMS 1. All experiments contained an untreated control (only water added) and were arranged in completely randomized designs.

Fungi were pipetted onto the soil surface of each cup in 0.5 and 1.4 ml of water and 0.05% Tween 80, respectively, so the final moisture was standardized at field capacity (14%). In the first fungus assay (Assay 3 trial 1), the application rate was approximately 7,950 conidia per $cm^2$, but, due to low mortality, 15,900 conidia per $cm^2$ were applied thereafter. After inoculation, fungus experiments were incubated at 25° C., and mortality due to fungi, i.e., signs of mycosis (Tanada Y., and H. K. Kaya, Insect Pathology (1993), Academic Press, San Diego, Calif.), was recorded every one-three days beginning 5 days post-inoculation. Preliminary experimentation indicated it was not necessary to make observations prior to 5 days. The rates of application were based on previous laboratory experiments that showed differences among strains at similar rates (Harrison, R. D., et al., Relative susceptibility of pecan weevil fourth instars and adults to selected isolates of *Beauveria bassiana*, Biological Control, 3: 34-38 (1993)).

Data Analysis: Virulence assays were analyzed using analysis of variance; if the F value was significant ($\alpha=0.05$) then means were differentiated by LSMEANS (SAS, 1985, SAS Users Guide: Version 5 ed., SAS Institute, Cary, N.C.). In the fungus assays, mycosis was recorded through time, therefore analysis of variance was applied for each day separately as well as over the entire experimental period (repeated measure analysis, Proc Mixed, SAS 1985) (McCoy, C. W., et al.,Entomopathogenic nematodes and other natural enemies as mortality factors for larvae of *Diaprepes abbreviatus* (Coleoptera: Curculionidae), Biol. Control, 19: 182-190 (2000); Shapiro, D. I., et al., Effects of soil type on virulence and persistence of entomopathogenic nematodes in relation to control of *Diaprepes abbreviatus*, Environ. Entomol., 29: 1083-1087 (2000)). In each assay, trials were combined for analysis except for Assay 3 because it had different application rates of conidia in each of the trials.

Results:

Entomopathogenic fungi were isolated from 16/21 of the orchards (76.2%) and 21/105 of the sites (20.0%) tested in Arkansas, Georgia, Louisiana and Mississippi. The entomopathogenic fungi isolated were *B. bassiana* and *M. anisopliae* var. *anisopliae*. *Beauveria bassiana* was found in 12 orchards (57.1%) and 15 sites (14.3%) whereas *M. anisopliae* was isolated in 5 orchards (23.8%) and 6 sites (5.7%). Some sites yielded more than one isolate.

Significant differences in virulence were detected among the fungal isolates. A number of isolates caused greater *C. caryae* mortality than the control and the standard (Mycotrol®) (Tables 1-5). In Assay 3 trial 1, no differences in *C. caryae* larval mortality were detected among treatments on any given day (P>0.05) (Table 1). When averaged over the entire experimental period, however, two isolates (BbMS1 and BbGA2) caused significantly greater *C. caryae* mortality compared with the control (F=12.77; df=7,182; P=0.0001) (Table 1). Additionally, the overall average mortality caused by each of the new fungal isolates, except for BbAR1 and BbMS2, were greater than the standard (Table 1). In the $2^{nd}$ trial of Assay 3, *B. bassiana* isolate BbGA2 caused greater mortality than the control seven days post-inoculation (F=3.91; df=7,16; P=0.011); no other significant differences were detected when data were analyzed by day (P<0.05) (Table 2). When averaged over the entire experimental period, all the fungal isolates except BbAR1 caused greater *C. caryae* mortality relative to the control, and BbGA2 caused greater mortality than all other isolates (F=11.89; df=7,154; P=0.0001) (Table 2).

In Assay 4, on days 12-14 a number of isolates caused greater mortality than the control (P>0.05) (Table 3). When averaged over the entire experimental period, all the new fungal isolates caused greater mortality than the control and standard, which were not different from each other (F=13.82; df=9,294; P=0.0001) (Table 3).

In Assay 5, a number of isolates caused greater mortality than the control and Mycotrol® between eight and 15 days post inoculation (P<0.05) (Table 4). When analyzed over the whole experimental period, BbMS1 caused greater mortality than all other isolates followed by BbGA6 (F=51.98; df=7,280; P=0.0001) (Table 4).

In Assay 6, when analyzed by day, BbMS1 and BbLA3 caused greater mortality than the control earlier and more consistently than any other isolates (Table 5) (P<0.05). When analyzed over the whole experimental period, BbMS1 caused greater mortality among isolates followed by BbMS3 (F=83.88; df=6,156; P=0.0001) (Table 5).

To summarize the fungus virulence assays, isolates BbGA2 and MaLA4 may be considered the most virulent because they are the only isolates that caused greater mortality than all other isolates in at least one assay, and in all assays no other isolate caused greater mortality than they did (Tables 1-5). Other isolates that showed relatively high virulence include BbMS1, BbGA6, and BbLA3 (Tables 1-5). The standard, Mycotrol®, caused greater mortality than the control in two of the four fungal assays.

Another experiment was conducted with *Metarhizium anisopliae* isolate MaLA4. We applied fungal conidia to soil in 30 ml plastic cups containing a single pecan weevil larva each, as described previously in our methods. There were 3 replicates of 10 cups for each treatment. Data are shown in Table 6; at nineteen days after inoculation the larval mortality was significantly greater for *Metarhizium anisopliae* isolate MaLA4 in comparison to the control.

Discussion:

The fungal standard, Mycotrol®, had relatively low virulence against *C. caryae* larvae, perhaps due to a dosage effect. For example, the virulence of Mycotrol® to adult *C. caryae* was demonstrated in two field trials in which greater than 70% of weevils were killed by Mycotrol® within one week of application (unpublished data). The application rates in the field study were >10 fold those used in the current study. If we had used a higher application rate in the current study mortality then rates likely would have been greater; thus it is not necessary to conclude that Mycotrol® is not pathogenic to *C. caryae* larvae (at least two assays prove otherwise) but rather that the new isolates are more virulent.

Several fungal isolates were highly virulent and can be used for microbial control of *C. caryae* larvae. Previous studies have indicated greater virulence in *B. bassiana* isolates compared with *M. anisopliae* (Tedders, W. L., et al., Pecan weevil: suppression of larvae with the fungi *Metarhizium anisopliae* and *Beauveria bassiana* and the nematode *Neoaplectana dutkyi,* J. Econ. Entomol., 66: 723-725 (1973); Gottwald, T. R., and W. L. Tedders, Suppression of pecan weevil (Coleoptera: Curculionidae) populations with entomopathogenic fungi, Environ. Entomol., 12: 471-474 (1983)). Our findings, however, surprisingly indicate that some *M. anisopliae* isolates can be equal or greater in virulence. The relatively low *C. caryae* mortality caused by all isolates in Assay 3 trial 1 was clearly due to the lower application rate in the trial; despite the low mortality, the assay was useful in distinguishing virulence among the isolates. The application rate used in most of our assays (15,900 per $cm^2$) is more than 10 fold less than recommended field rates (e.g., 2-8×$10^5$ per $cm^2$). It was very surprising that a number of isolates caused greater than 60% *C. caryae* mortality with such a low rate. Two isolates in particular, BbGA2 and MaLA4, were consistently among the most virulent.

The fungal isolates NRRL 30593, NRRL 30594, NRRL 30601, and NRRL 30600 were tested versus three additional insects of diverse classification: the *diaprepes* root weevil, *Diaprepes abbreviatus* (L.); fall armyworm, *Spodoptera frugiperda,* (J. E. Smith); and fire ants, *Solenopsis invicta,* Buren. *Diaprepes abbreviatus* is a major pest of a number of commodities including ornamental plants and citrus, and the insect is classified in the same order and family as pecan weevil (Coleoptera: Curculionidae). *Spodoptera frugiperda* is a major pest of various grains (e.g., corn) and vegetables, and the insect is classified in the order Lepidoptera, family Noctuidae. Fire ants were introduced into the United States from South America and have since become a major pest of health and economic significance, the insect is in the order Hymenoptera, family Formicidae.

For *D. abbreviatus* the virulence of fungal strains was tested using the same experimental approach as described above in the pecan weevil virulence. The rate of application was 2 million conidia per cup (one insect per cup) with 3 replicates of 10 cups per treatment. Mortality was recorded 21 days after application following incubation at 25° C. Mean mortality was analyzed by ANOVA and Least Square Means (LSD) (means were arcsine transformed prior to analysis). Results are displayed in FIG. 1. Isolate 30594 caused greater mortality than the control (only water added) and the commercial strain GHA.

For the fire ant assays, filter paper was placed in the bottom of a 5-cm Petri dish and approximately 50 worker ants were added to each dish. The dish was sprayed with 1 ml using a Solo Spraystar 460. The treatments were $10^4$, $10^5$, and $10^6$ conidia per dish of either NRRL 30593 or NRRL 30594 (plus an untreated control). The filter paper, with ants, was transferred right away to a 17×8×4 cm plastic container with 30 g of sand in the bottom, with a small dish of water and a dead cricket for food. Ant mortality was recorded after 10 days. There were three replicates of each treatment. Treatment effects were analyzed by ANOVA of mean mortality (following arcsine transformation) and LSD tests. Results are displayed in FIGS. 2 and 3. For both fungi tested, the $10^6$ concentrations caused greater mortality than the control (lower concentrations were not statistically different from the control). The *M. anisopliae* isolate (30594) caused numerically higher mortality than the *B. bassiana* (30593).

In *S. frugiperda* assays, first and third instars were exposed to a single concentration of fungal conidia on a bean leaf disk. Circular bean leaf disks, measuring 25 mm diam, were cut from snap bean plant leaves. A suspension of fungal conidia of each of the fungal strains was prepared by scraping SDAY cultures of each and mixing in sterile distilled water+Tween 80. This was evenly spread over the upper and lower surfaces of the disk to create a concentration of ~6,500 conidia/$mm^2$ on the leaf surface. In tests with first instars, neonates were placed on the treated disk, which was maintained on moistened filter paper in a Petri dish. In tests with third instars, 3 larvae were placed on one treated disk. After 24 h, larvae were individually transferred to 30-mL clear plastic cups containing a pinto bean artificial diet. A total of 60 larvae were tested for each fungal strain. Mortality was observed and confirmed 10 days after initial exposure. Results in Table 7 indicate all isolates are pathogenic to *S. frugiperda.*

All of the references cited herein are incorporated by reference in their entirety. Also incorporated by reference in their entirety are the following U.S. Pat. Nos.: 6,280,723; 6,261,553; 6,254,864; 5,900,234; 5,516,513; 5,413,784; and 4,925,663. Also incorporated by reference in its entirety is the following: L. A. Lacey [ed.] Manual of techniques in insect pathology (1997, 2000), Academic Press, San Diego).

Thus, in view of the above, the present invention concerns (in part) the following:

A biologically pure culture of fungus selected from the group consisting of *Beauveria bassiana* having all the identifying characteristics of NRRL 30593, *Metarhizium anisopliae* having all the identifying characteristics of NRRL 30594, *Beauveria bassiana* having all the identifying characteristics of NRRL 30601, *Beauveria bassiana* having all the identifying characteristics of NRRL 30600, and mixtures thereof.

A biologically pure culture of fungus selected from the group consisting of *Beauveria bassiana* having all the identifying characteristics of NRRL 30593, *Metarhizium anisopliae* having all the identifying characteristics of NRRL 30594, *Beauveria bassiana* having all the identifying characteristics of NRRL 30601, and *Beauveria bassiana* having all the identifying characteristics of NRRL 30600.

A biologically pure culture of *Beauveria bassiana* having all the identifying characteristics (e.g., virulence against pecan weevils) of NRRL 30593.

A biologically pure culture of *Metarhizium anisopliae* having all the identifying characteristics (e.g., virulence against pecan weevils) of NRRL 30594.

A biologically pure culture of *Beauveria bassiana* having all the identifying characteristics (e.g., virulence against pecan weevils) of NRRL 30601.

A biologically pure culture of *Beauveria bassiana* having all the identifying characteristics (e.g., virulence against pecan weevils) of NRRL 30600.

A biologically pure culture of fungi comprising at least two members selected from the group consisting of *Beauveria bassiana* having all the identifying characteristics of *Beauveria bassiana* NRRL 30593, *Metarhizium anisopliae* having all the identifying characteristics of *Metarhizium anisopliae* NRRL 30594, *Beauveria bassiana* having all the identifying characteristics of *Beauveria bassiana* NRRL 30601, and *Beauveria bassiana* having all the identifying characteristics of *Beauveria bassiana* NRRL 30600.

A biologically pure culture of fungus selected from the group consisting of *Beauveria bassiana* NRRL 30593, *Metarhizium anisopliae* NRRL 30594, *Beauveria bassiana* NRRL 30601, *Beauveria bassiana* NRRL 30600, and mixtures thereof.

A biologically pure culture of *Beauveria bassiana* NRRL 30593.

A biologically pure culture of *Metarhizium anisopliae* NRRL 30594.

A biologically pure culture of *Beauveria bassiana* NRRL 30601.

A biologically pure culture of *Beauveria bassiana* NRRL 30600.

A biologically pure culture of fungus selected from the group consisting of *Beauveria bassiana* NRRL 30593, *Metarhizium anisopliae* NRRL 30594, *Beauveria bassiana* NRRL 30601, and *Beauveria bassiana* NRRL 30600.

*Beauveria bassiana* NRRL 30593.
*Metarhizium anisopliae* NRRL 30594.
*Beauveria bassiana* NRRL 30601.
*Beauveria bassiana* NRRL 30600.

A biopesticidal composition for controlling insects (e.g., pecan weevils, the *diaprepes* root weevil, fall armyworm, fire ants), comprising (or consisting essentially of or consisting of) an agriculturally acceptable carrier and an effective insect (e.g., pecan weevils, the *diaprepes* root weevil, fall armyworm, fire ants) biopesticidal amount of at least one fungus selected from the group consisting of *Beauveria bassiana* having the identifying characteristics of *Beauveria bassiana* NRRL 30593, *Metarhizium anisopliae* having the identifying characteristics of *Metarhizium anisopliae* NRRL 30594, *Beauveria bassiana* having the identifying characteristics of *Beauveria bassiana* NRRL 30601, *Beauveria bassiana* having the identifying characteristics of *Beauveria bassiana* NRRL 30600, and mixtures thereof.

A method for controlling insects (e.g., pecan weevils, the *diaprepes* root weevil, fall armyworm, fire ants), comprising (or consisting essentially of or consisting of) applying an effective insect biopesticidal amount of the above composition to said insects or to the plants, areas or substrates (e.g., soil) infested with said insects.

The above method, wherein said insects are adults or larvae.

The above method, wherein said insects are pecan weevils (e.g., adults or larvae).

A biopesticidal composition for controlling insects (e.g., pecan weevils, the *diaprepes* root weevil, fall armyworm, fire ants), comprising (or consisting essentially of or consisting of) an agriculturally acceptable carrier and an effective insect (e.g., pecan weevils, the *diaprepes* root weevil, fall armyworm, fire ants) biopesticidal amount of at least one fungus selected from the group consisting of *Beauveria bassiana* NRRL 30593, *Metarhizium anisopliae* NRRL 30594, *Beauveria bassiana* NRRL 30601, *Beauveria bassiana* NRRL 30600, and mixtures thereof.

A method for controlling insects (e.g., pecan weevils, the *diaprepes* root weevil, fall armyworm, fire ants), comprising (or consisting essentially of or consisting of) applying an effective insect biopesticidal amount of the above composition to said insects or to the plants, areas or substrates (e.g., soil) infested with said insects.

The above method, wherein said insects are adults or larvae.

The above method, wherein said insects are pecan weevils (e.g., adults or larvae).

Other embodiments of the invention will be apparent to those skilled in the art from a consideration of this specification or practice of the invention disclosed herein. It is intended that the specification and examples be considered as exemplary only, with the true scope and spirit of the invention being indicated by the following claims.

TABLE 1

Mean percentage (se) of *Curculio caryae* larvae infected with *Beauveria bassiana* isolates from soil in Southeastern pecan orchards (Assay 3, Trial 1)[a].

| Isolate | Days Post Inoculation | | | | | | | | Average[b] |
|---|---|---|---|---|---|---|---|---|---|
| | 7 | 8 | 9 | 10 | 11 | 12 | 13 | 14 | |
| Control | 3.3 ± 3.3a | 3.3 ± 3.3a | 3.3 ± 3.3a | 6.7 ± 3.3a | 6.7 ± 3.3a | 6.7 ± 3.3a | 6.7 ± 3.3a | 10.0 ± 5.8a | 4.6 ± 0.89bc |
| Mycotrol® | 0 ± 0a | 0 ± 0a | 3.3 ± 3.3a | 3.3 ± 3.3a | 3.3 ± 3.3a | 3.3 ± 3.3a | 3.3 ± 3.3a | 3.3 ± 3.3a | 1.54 ± 0.59d |
| BbAR1 | 0 ± 0a | 0 ± 0a | 0 ± 0a | 0 ± 0a | 0 ± 0a | 0 ± 0a | 3.3 ± 3.3a | 6.7 ± 6.7a | 0.77 ± 0.57d |
| BbGA1 | 3.3 ± 3.3a | 3.3 ± 3.3a | 3.3 ± 3.3a | 3.3 ± 3.3a | 10.0 ± 5.8a | 13.3 ± 3.3a | 13.3 ± 3.3a | 13.3 ± 3.3a | 5.90 ± 1.08b |
| BbGA2 | 13.3 ± 3.3a | 13.3 ± 3.3a | 13.3 ± 3.3a | 13.3 ± 3.3a | 13.3 ± 3.3a | 13.3 ± 3.3a | 13.3 ± 3.3a | 16.7 ± 6.7a | 9.74 ± 1.19a |
| BbMS1 | 13.3 ± 6.7a | 13.3 ± 6.7a | 13.3 ± 6.7a | 10.0 ± 10.0a | 16.7 ± 8.8a | 20.0 ± 11.5a | 20.0 ± 11.5a | 23.3 ± 12.0a | 12.31 ± 2.16a |

TABLE 1-continued

Mean percentage (se) of *Curculio caryae* larvae infected with *Beauveria bassiana* isolates from soil in Southeastern pecan orchards (Assay 3, Trial 1)[a].

| Isolate | Days Post Inoculation | | | | | | | | Average[b] |
|---|---|---|---|---|---|---|---|---|---|
| | 7 | 8 | 9 | 10 | 11 | 12 | 13 | 14 | |
| BbMS2 | 3.3 ± 3.3a | 3.3 ± 3.3a | 3.3 ± 3.3a | 3.3 ± 3.3a | 3.3 ± 3.3a | 3.3 ± 3.3a | 3.3 ± 3.3a | 10.0 ± 5.8a | 2.82 ± 0.82cd |
| BbMS3 | 3.3 ± 3.3a | 3.3 ± 3.3a | 16.7 ± 6.7a | 16.7 ± 6.7a | 16.7 ± 6.7a | 16.7 ± 6.7a | 20.0 ± 5.8a | 20.0 ± 5.8a | 8.72 ± 1.73ab |

[a]Numbers followed by different letters within each column are statistically different ($\alpha = 0.05$). No significant differences were detected 5-7 d post inoculation (data not shown).
[b]Average of observations 5-14 d post inoculation.

TABLE 2

Mean percentage (se) of *Curculio caryae* larvae infected with *Beauveria bassiana* isolates from soil in southeastern pecan orchards (Assay 3, trial 2)[a].

| Isolate | Days Post Inoculation | | | | | | | Average[b] |
|---|---|---|---|---|---|---|---|---|
| | 7 | 10 | 11 | 12 | 13 | 14 | 17 | |
| Control | 3.3 ± 3.3b | 6.7 ± 6.7a | 6.7 ± 6.7a | 6.7 ± 6.7a | 6.7 ± 6.7a | 6.7 ± 6.7a | 16.0 ± 12.0a | 6.1 ± 1.7e |
| Mycotrol® | 3.3 ± 3.3b | 13.3 ± 13.3a | 16.7 ± 12.0a | 23.3 ± 13.3a | 23.3 ± 13.3a | 26.7 ± 12.0a | 26.7 ± 12.0a | 13.3 ± 3.0c |
| BbAR1 | 0 ± 0b | 3.3 ± 3.3a | 6.7 ± 3.3a | 6.7 ± 3.3a | 10.0 ± 0a | 16.7 ± 3.3a | 33.3 ± 12.0a | 7.0 ± 2.0de |
| BbGA1 | 0 ± 0b | 6.7 ± 6.7a | 6.7 ± 6.7a | 16.7 ± 8.8a | 26.7 ± 8.8a | 36.7 ± 8.8a | 46.7 ± 13.3a | 12.7 ± 3.3cd |
| BbGA2 | 13.3 ± 3.3a | 23.3 ± 8.8a | 23.3 ± 8.8a | 30.0 ± 5.8a | 33.3 ± 3.3a | 33.3 ± 3.3a | 60.0 ± 5.8a | 23.3 ± 3.0a |
| BbMS1 | 0 ± 0b | 6.7 ± 3.3a | 10.0 ± 5.8a | 13.3 ± 6.7a | 16.7 ± 8.8a | 33.3 ± 8.8a | 56.7 ± 8.8a | 12.4 ± 3.3cd |
| BbMS2 | 0 ± 0b | 13.3 ± 8.8a | 33.3 ± 3.3a | 36.7 ± 3.3a | 50.0 ± 5.8a | 50.0 ± 5.8a | 60.0 ± 5.8a | 22.1 ± 4.2b |
| BbMS3 | 6.7 ± 3.3ab | 13.3 ± 8.8a | 13.3 ± 8.8a | 16.7 ± 12.0a | 23.3 ± 14.5a | 23.3 ± 14.5a | 33.3 ± 20.3a | 12.7 ± 3.1c |

[a]Numbers followed by different letters within each column are statistically different ($\alpha = 0.05$). No significant differences were detected 5-6 d post inoculation (data not shown).
[b]Average of observations 5-17 d post inoculation.

TABLE 3

Mean percentage (±se) of *Curculio caryae* larvae infected with *Beauveria bassiana* or *Metarhizium anisopliae* isolates from soil in Southeastern US pecan orchards (Assay 4)[a.]

| Isolate | Days Post Inoculation | | | | | | | Average |
|---|---|---|---|---|---|---|---|---|
| | 5 | 6 | 7 | 8 | 12 | 13 | 14 | |
| Control | 4.0 ± 2.6a | 5.7 ± 2.6bc | 8.1 ± 4.6bc | 9.8 ± 5.0bc | 14.8 ± 4.9cd | 16.4 ± 5.5d | 22.1 ± 5.1d | 11.5 ± 1.8c |
| Mycotrol® | 1.7 ± 1.7a | 3.3 ± 3.3c | 3.3 ± 3.3c | 3.3 ± 3.3c | 10.7 ± 5.2d | 15.7 ± 6.1d | 25.7 ± 12.4d | 9.5 ± 32.5c |
| BbMS1 | 3.3 ± 2.1a | 5.0 ± 3.4bc | 6.7 ± 4.9bc | 11.7 ± 7bc | 34.8 ± 12.3bc | 39.5 ± 10.4c | 46.7 ± 9.3bc | 21.1 ± 3.9b |
| MaLA5 | 6.7 ± 3.3a | 6.7 ± 4.2bc | 12.4 ± 4.8bc | 14.8 ± 4.1ab | 33.8 ± 10.9bc | 40.2 ± 8.6bc | 46.7 ± 8.6bc | 23.0 ± 3.4b |
| MaLA7 | 3.3 ± 2.1a | 5.0 ± 3.1bc | 5.0 ± 3.4c | 11.4 ± 2.7bc | 51.0 ± 7.0b | 60.7 ± 9.2ab | 60.7 ± 9.2abc | 28.2 ± 4.5b |
| MaLA8 | 6.7 ± 3.3a | 6.7 ± 3.3bc | 6.7 ± 3.3bc | 10.0 ± 0abc | 30.0 ± 0bc | 40.0 ± 0bc | 50.0 ± 0bc | 21.4 ± 3.9b |
| MaLA6 | 1.7 ± 1.7a | 10.0 ± 6.3bc | 13.3 ± 8.0bc | 19.0 ± 8.6ab | 40.5 ± 12.4b | 51.0 ± 10.8bc | 54.3 ± 12.3bc | 27.1 ± 4.5b |
| BbLA1 | 1.7 ± 1.7a | 5.7 ± 2.6bc | 5.7 ± 2.6bc | 10.7 ± 5.2bc | 51.4 ± 10.1b | 53.8 ± 10.6bc | 64.3 ± 8.3ab | 27.6 ± 4.6b |

[a]Numbers followed by different letters within each column are statistically different ($\alpha = 0.05$).

TABLE 4

Mean percentage (se) of *Curculio caryae* larvae infected with *Beauveria bassiana* isolates from soil in Southeastern pecan orchards (Assay 5)[a]

| Isolate | Days Post Inoculation | | | | | | | | Average[b] |
|---|---|---|---|---|---|---|---|---|---|
| | 8 | 9 | 10 | 11 | 12 | 13 | 14 | 15 | |
| Control | 3.3 ± 3.3.3c | 6.7 ± 3.33bc | 13.3 ± 3.3b | 16.7 ± 3.3abc | 16.7 ± 3.3bc | 16.7 ± 3.3bc | 16.7 ± 3.3b | 20.0 ± 0.0c | 9.0 ± 1.3d |
| Mycotrol® | 6.7 ± 3.3bc | 6.7 ± 3.3bc | 6.7 ± 3.3bc | 6.7 ± 3.3cd | 6.7 ± 3.3cd | 20.0 ± 5.8bc | 20.0 ± 5.8b | 20.0 ± 5.8c | 7.6 ± 1.4d |
| BbMS1 | 23.3 ± 3.3a | 33.3 ± 8.8a | 40.0 ± 5.8a | 40.0 ± 5.8a | 46.7 ± 8.8a | 53.33 ± 6.7a | 56.7 ± 3.3a | 73.3 ± 13.3a | 32.6 ± 3.3a |
| BbGA3 | 16.7 ± 6.7ab | 16.7 ± 6.7ab | 16.7 ± 6.7ab | 16.7 ± 6.7abc | 16.7 ± 6.7bc | 16.7 ± 6.7bc | 16.7 ± 6.7b | 16.7 ± 6.7c | 14.0 ± 1.6c |
| BbGA4 | 10.0 ± 4.5abc | 8.3 ± 4.8bc | 11.7 ± 4.8bc | 16.7 ± 4.9bc | 15.0 ± 5.6bc | 18.3 ± 6.0bc | 20.0 ± 6.3b | 26.7 ± 5.8bc | 10.7 ± 1.4d |

TABLE 4-continued

Mean percentage (se) of *Curculio caryae* larvae infected with *Beauveria bassiana* isolates from soil in Southeastern pecan orchards (Assay 5)[a]

| Isolate | 8 | 9 | 10 | 11 | 12 | 13 | 14 | 15 | Average[b] |
|---|---|---|---|---|---|---|---|---|---|
| BbGA6 | 18.3 ± 4.0ab | 18.3 ± 4.01ab | 21.7 ± 5.4ab | 25.0 ± 5.6ab | 33.3 ± 4.9ab | 41.7 ± 5.4ab | 45.0 ± 5.6a | 48.3 ± 4.0b | 21.7 ± 1.9b |
| BbGA7 | 3.3 ± 3.3c | 6.7 ± 3.3bc | 6.7 ± 3.3bc | 6.7 ± 3.3cd | 6.7 ± 3.3cd | 13.3 ± 8.8c | 20.0 ± 10.0b | 20.0 ± 10.0c | 6.7 ± 1.5d |
| BbGA8 | 0.0 ± 0.0c | 0.0 ± 0.0 c | 0.0 ± 0.0c | 0.0 ± 0.0d | 0.0 ± 0.0d | 0.0 ± 0.0d | 0.0 ± 0.0c | 0.0 ± 0.0d | 0.0 ± 0.0e |

[a]Numbers followed by different letters within each column are statistically different ($\alpha = 0.05$). No significant differences were detected 5-7 d post inoculation (data not shown).
[b]Average of observations 3-15 d post inoculation.

TABLE 5

Mean percentage (se) of *Curculio caryae* larvae infected with *Beauveria bassiana* or *Metarhizium anisopliae* isolates from soil in Southeastern pecan orchards (Assay 6)[a]

| Isolate | 7 | 8 | 9 | 10 | 11 | 12 | 13 | 14 | Average[b] |
|---|---|---|---|---|---|---|---|---|---|
| Control | 16.7 ± 12.0b | 16.7 ± 12.0b | 20.0 ± 11.6bc | 20.0 ± 11.6bc | 20.0 ± 11.6bcd | 20.0 ± 11.6cd | 20.0 ± 11.6cd | 23.3 ± 14.5cd | 15.4 ± 2.6d |
| Mycotrol® | 23.3 ± 8.8ab | 26.7 ± 6.7ab | 30.0 ± 10.0ab | 36.7 ± 8.8a | 46.7 ± 12.0ab | 46.7 ± 12.0bc | 46.7 ± 12.0bc | 46.7 ± 12.0bc | 28.2 ± 3.4c |
| BbMS1 | 50.0 ± 10.0a | 53.3 ± 8.8a | 60.0 ± 10.0a | 63.3 ± 6.7a | 70.0 ± 5.8a | 96.7 ± 3.3a | 96.7 ± 3.3a | 96.7 ± 3.3a | 53.1 ± 5.2a |
| BbLA2 | 20.0 ± 5.8b | 30.0 ± 11.5b | 30.0 ± 11.6ab | 30.0 ± 11.6ab | 33.3 ± 8.8abc | 33.3 ± 8.8bc | 33.3 ± 8.8bcd | 33.3 ± 8.8cd | 20.5 ± 2.9d |
| BbLA3 | 33.3 ± 3.3ab | 33.3 ± 3.3ab | 53.3 ± 12.0a | 53.3 ± 12.0a | 53.3 ± 12.0a | 70.0 ± 15.3b | 73.3 ± 12.0ab | 76.7 ± 14.5ab | 42.1 ± 4.2b |
| MaLA2 | 0.0 ± 0.0c | 0.0 ± 0.0c | 6.7 ± 3.3bc | 10.0 ± 5.8bc | 13.3 ± 8.8cd | 16.7 ± 8.8cd | 16.7 ± 8.8d | 16.7 ± 8.8cd | 6.2 ± 1.7d |
| MaLA3 | 0.0 ± 0.0c | 0.0 ± 0.0c | 0.0 ± 0.0c | 0.0 ± 0.0c | 0.0 ± 0.0d | 0.0 ± 0.0d | 6.7 ± 6.7cd | 6.7 ± 6.7d | 1.0 ± 0.7d |

[a]Numbers followed by different letters within each column are statistically different ($\alpha = 0.05$). No significant differences were detected between the control and fungal isolates 5-7 d post inoculation (data not shown).
[b]Average of observations 3-14 d post inoculation.

TABLE 6

Mean percentage (±se) mortality of *Curculio caryae* larvae following exposure to *Metarhizium anisopliae* culture MaLA4.

| Isolate | 6 | 9 | 12 | 16 | 19 | Average |
|---|---|---|---|---|---|---|
| Control | 6.7 ± 3.3a | 13.3 ± 3.3a | 13.3 ± 3.3a | 23.3 ± 3.3a | 23.3 ± 3.3b | 16.0 ± 2.1a |
| Ma | 3.3 ± 3.3a | 10.0 ± 3.4a | 23.3 ± 3.3a | 56.7 ± 6.7a | 70.0 ± 5.8a | 32.7 ± 7.3a |

Control = no fungus applied, Ma = *M. anisopliae* culture MaLA4. Numbers followed by different letters within each column are statistically different ($\alpha = 0.05$, LSD). Rate of application was ca. 79,500 conidia per $cm^2$.

TABLE 7

Fall armyworm larval mortality following exposure to fungal strains of *Beauveria bassiana* and *Metarhizium anisopliae*.

| Fungus | Strain | First Instar Corrected % Mortality | Third Instar Corrected % Mortality |
|---|---|---|---|
| *B. bassiana* | 30601 | 94.3% | 85.9% |
| | 30593 | 90.6% | 82.6% |
| | 30600 | 83.0% | 80.7% |
| | GHA | 90.6% | 87.7% |
| *M. anisopliae* | 30594 | 84.9% | 82.6% |

We claim:

1. A biologically pure culture of fungus selected from the group consisting of *Beauveria bassiana* NRRL 30593, *Metarhizium anisopliae* NRRL 30594, *Beauveria bassiana* NRRL 30601, *Beauveria bassiana* NRRL 30600, and mixtures thereof.

2. The biologically pure culture of fungus according to claim 1, wherein said fungus is *Beauveria bassiana* NRRL 30593.

3. The biologically pure culture of fungus according to claim 1, wherein said fungus is *Metarhizium anisopliae* NRRL 30594.

4. The biologically pure culture of fungus according to claim 1, wherein said fungus is *Beauveria bassiana* NRRL 30601.

5. The biologically pure culture of fungus according to claim 1, wherein said fungus is *Beauveria bassiana* NRRL 30600.

6. A biopesticidal composition for controlling insects, comprising an agriculturally acceptable carrier and an effective insect biopesticidal amount of at least one fungus selected from the group consisting of *Beauveria bassiana* NRRL 30593, *Metarhizium anisopliae* NRRL 30594, *Beauveria bassiana* NRRL 30601, *Beauveria bassiana* NRRL 30600, and mixtures thereof; wherein said insects are selected from the group consisting of pecan weevils, the *diaprepes* root weevil, fall armyworm, fire ants, and mixtures thereof.

7. The biopesticidal composition for controlling insects according to claim 6, wherein said fungus is *Beauveria bassiana* NRRL 30593.

8. The biopesticidal composition for controlling insects according to claim 6, wherein said fungus is *Metarhizium anisopliae* NRRL 30594.

9. The biopesticidal composition for controlling insects according to claim 6, wherein said fungus is *Beauveria bassiana* NRRL 30601.

10. The biopesticidal composition for controlling insects according to claim 6, wherein said fungus is *Beauvena bassiana* NRRL 30600.

11. A method for controlling insects, comprising applying an effective insect biopesticidal amount of the composition according to claim 6 to said insects or to the plants, areas or substrates infested with said insects; wherein said insects are selected from the group consisting of pecan weevils, the *diaprepes* root weevil, fall armyworm, fire ants, and mixtures thereof.

12. The method according to claim 11, wherein said insects are pecan weevils.

13. The method according to claim 12, wherein said pecan weevils are in the form of adults.

14. The method according to claim 12, wherein said pecan weevils are in the form of larvae.

* * * * *